United States Patent [19]

Lawford

[11] Patent Number: 4,731,329

[45] Date of Patent: * Mar. 15, 1988

[54] ETHANOL PRODUCTION BY HIGH PERFORMANCE BACTERIAL FERMENTATION

[75] Inventor: Hugh G. Lawford, Mississauga, Canada

[73] Assignee: George Weston Ltd., Toronto, Canada

[*] Notice: The portion of the term of this patent subsequent to Mar. 3, 2004 has been disclaimed.

[21] Appl. No.: 944,072

[22] Filed: Dec. 22, 1986

Related U.S. Application Data

[63] Continuation of Ser. No. 641,364, Aug. 15, 1984, Pat. No. 4,647,534, which is a continuation of Ser. No. 217,066, Sep. 16, 1980, abandoned, which is a continuation-in-part of Ser. No. 184,508, May 9, 1980, abandoned.

[51] Int. Cl.$^4$ ............................................... C12P 7/14
[52] U.S. Cl. .................................... 435/162; 435/813
[58] Field of Search ............... 435/161, 162, 163, 164, 435/165, 813

[56] References Cited

U.S. PATENT DOCUMENTS 1,920,735  8/1933  Bakonyi .............................. 435/62

OTHER PUBLICATIONS

Rogers et al, "High Productivity Ethanol Fermentations with Zymomonas Mobilis", Process Biochemistry, Aug.–Sep. (1980), pp. 9–11.

Flickinger, "Current Research on Conversion of Cellulose Carbohydrates into Liquid Fuels", Biotech. & Bioeng., vol. XXII (1980), pp. 27–48.

Belaich, "Uncoupling in Bacterial Growth: Effect of Pantothenate Starvation on Growth of Z. Mobilis", J. Gen. Microbiol., vol. 70 (1972), pp. 179–185.

*Primary Examiner*—R. B. Penland
*Attorney, Agent, or Firm*—Finnegan, Henderson, Farabow, Garrett & Dunner

[57] ABSTRACT

The present invention is directed to the preparation of ethanol by bacterial fermentation. It makes use of a microorganism capable of producing ethanol and the process is carried out in two stages. In the first stage a bacterial cell suspension is produced together with ethanol in an ethanol concentration range that does not substantially inhibit production of the bacterial cells in a medium containing a source of nitrogen and a source of carbon. Ethanol is then produced in the absence of substantial bacterial cell production by the addition of fermentable sugar to the bacterial cell suspension which is produced in the first stage. The preferred microorganism is a member of the genus Zymomonas.

10 Claims, No Drawings

ETHANOL PRODUCTION BY HIGH PERFORMANCE BACTERIAL FERMENTATION

This application is a continuation of application Ser. No. 641,364, filed Aug. 15, 1984, now U.S. Pat. No. 4,647,534, issued Mar. 3, 1987, which is a continuation of application Ser. No. 217,066, filed Sept. 16, 1980, now abandoned, which in turn is a continuation-in-part of application Ser. No. 184,508, filed Sept. 5, 1985, now abandoned.

The present invention relates to a process for the production of ethanol by fermentation. In particular it relates to the production of ethanol by a process of bacterial fermentation, in which there is improved fermentation efficiency and product yield as compared to prior art methods.

The traditional process of fermentation is carried out in a conventional batch operation utilizing yeast as the fermenting organism. To increase the efficiency a variation of the batch operation occasionally includes recycling of the yeast cells by systems such as sedimentation, centrifugation, or ultrafiltration. Normally this batch operation is conducted in two stages. The first stage involves propagation of the yeast and is referred to as the growth stage. The second stage involves the anaerobic process of ethanol production which is accompanied by a depletion of the oxygen. Further propagation of the yeast occurs during the anaerobic process of ethanol production.

Typically, a yeast inoculum is prepared in stage one. The requirements for maximum yeast reproduction are adequate amounts of carbon, nitrogen, minerals and oxygen, a pH in the range of 3.5 to 4.5, and a temperature in the range of 29°-35° C. Aerobic growth conditions define a system for more efficient production of yeast but under which no ethanol is reproduced.

Stage two is the fermentation stage where the alcohol is actually produced by the yeast from the fermentable sugars. The yeast inoculum produced in stage (i) is used to seed a large fermenter previously filled with the substrate, which may be molasses, corn, etc., adjusted to the appropriate pH, temperature and sugar concentration. The inoculation rate can be 5 to 10 million cells per ml and during the fermentation the viable cell count can increase to 150-200 million cells per ml. Heat produced is controlled through the use of cooling coils. At these yeast levels, a final ethanol concentration of about 9 to 11% (v/v) can be obtained in 30 to 70 hours with batch fermentation. Increasing the yeast content, as is the case with cell recycle, can considerably reduce the time required for completion of the fermentation. For example, with a cell density of 800 to 1000 million cells per ml, it is possible to reduce the fermentation time to 4 to 10 hours.

It is recognized that, although conditions of strict anaerobiosis promote maximum production of ethanol, growth of yeast is suppressed. Inherent in this fermentation process is the coupling of growth with the rate of alcohol production. Consequently, in order to optimize ethanol production, either the degree of aeration must be finely controlled, or the medium must be supplied with growth-promoting supplements (for example, ergosterol or unsaturated fatty acids such as oleic acid).

Accordingly, the present invention describes a process for the production of ethanol by bacterial further that yeast fermentation. The process utilizes an organism which is capable of producing ethanol such as the bacterium Zymomonas as the fermenting organism. A number of different strains of *Zymomonas mobilis* may be used; for example ATCC 29191, ATCC 10988, etc. The process consists of two stages, an initial stage for the production of biomass, and a second stage for the production of ethanol. Unlike the prior art methods, the growth stage in this process occurs anaerobically and is accompanied by the production of ethanol. The fermentation stage of the *Z. mobilis* process resembles that of the prior art method in the respect that both occur under anaerobic conditions. However, in the bacterial process according to the present invention the production of ethanol is essentially uncoupled from growth (i.e. production of biomass). Thus, during the production of ethanol from such a "resting culture", only a small proportion of the substrate is converted to biomass and ethanol production is maximized. It follows that production of ethanol in the absence of growth with the bacterial process can be achieved simply by the addition of fermentable sugar and this system thereby is capable of yielding higher alcohol levels than the prior art process. In the prior art process high alcohol levels prevent growth and therefore alcohol production since this occurs only to a limited extent without growth.

Accordingly, the present invention comprises a process for producing ethanol by fermentation, which comprises culturing a microorganism capable of producing ethanol in two stages comprising (i) producing a bacterial cell suspension together with ethanol in an ethanol concentration range that does not substantially inhibit production of the microbial cells in a medium containing a source of nitrogen and a source of carbon and (ii) producing ethanol in the absence of bacterial cell production by the addition of fermentable sugar to the bacterial cell suspension produced in (i).

STAGE (i)

Growth of *Zymomonas mobilis* is conducted in an aqueous nutrient medium. The medium may be either a natural nutrient medium, a synthetic culture medium or a semi-synthetic culture medium as long as a suitable carbohydrate source and the essential nutrients for the growth of the microorganism are present. Although the growth stage in the process is normally used to generate sufficient quantities of biomass for the operation of the fermentation stage, the biomass may also be recycled with concomitant reduction in the essential nutrients required by the process.

In general, conditions which may be used to promote growth of *Z. mobilis* are: adequate carbon supply, adequate nitrogen supply, appropriate organic growth factors, adequate mineral supply, essentially anaerobic conditions, agitation of the culture, temperature in the range of 20°-40° C., and pH in the range of 4 to 8.

As carbon source for both the growth and the fermentation stages of the process various carbohydrates may be used. The carbohydrates include, for example, sugars such as glucose, fructose, sucrose; molasses; starch hydrolysate; cellulose hydrolysate; etc. These substances may be used either singly or in mixtures of two or more. As a nitrogen source, various kinds of inorganic or organic salts or compounds, for example ammonium salts such as ammonium chloride, ammonium sulfate, etc., or natural substances containing nitrogen, such as yeast extract, casein hydrolysate, corn steep liquor etc., or amino acids such as glutamic acid may be employed. These substances may also be used either singly or in combinations of two or more.

Inorganic compounds which may be added to the culture medium include magnesium sulfate, potassium monohydrogen phosphate, potassium dihydrogen phosphate, sodium chloride, magnesium sulfate, calcium chloride, iron chloride, magnesium chloride, zinc sulfate, cobalt chloride, copper chloride, borates, molybdates, etc.

Organic compounds which may be desirable for the operation of the process include, for example, vitamins such as biotin, calcium pantothenate, and the like, or organic acids such as citric acid or amino acids such as glutamic acid.

The microorganisms may be grown under the commonly-named operating conditions of either batch or continuous culture, with or without cell recycle in either case. The culturing or fermentation is conducted under essentially anaerobic conditions with agitation of a submerged culture, at a temperature of for example 20°-40° C., and a pH of for example 4.0 to 8.0. The preferred conditions are a temperature of about 30° C. and a pH of about 5.5. It may be desirable to add certain pH regulating agents to the medium during the course of culture fermentation, such as sodium hydroxide, hydrochloric acid, or the like.

STAGE (ii)

In the second stage of the process a broth of high ethanol content is produced by fermentation. Additional carbon in amounts such that the final ethanol concentration reaches the desired level is added to the spent broth containing the bacterial biomass. The carbon may be added either stepwise or continuously as a concentrated solution, but must never exceed approximately 6% (w/v). The options available as possible carbon sources for fermentation are described in stage (i) of the process.

The fermentation may be operated under the process conditions of so-called fed-batch or continuously, with or without cell recycle in either case. Process parameters for good production of ethanol include temperature in the range of 20°-40° C., pH in the range of 4 to 8, mixing of the fermenting broth, and essentially anaerobic conditions. The preferred temperature is about 28° to 33° C., and the preferred pH is about 5.5. It may be necessary or desirable to add pH regulating agents as described in stage (i). Anaerobic conditions may be maintained by bubbling a slow stream of nitrogen through the broth. Occassionally additional nutrients as described in stage (i) may be added to the fermenter.

The invention will be better understood by reference to the following examples which illustrate the invention.

EXAMPLE 1

1200 ml of a fermentation medium having the following compositions were placed in a 2 liter fermenter vessel:
Glucose: 10% (w/v)
Yeast extract (Difco): 1.5%
$KH_2PO_4$: 0.375%
$NH_4Cl$: 0.24%
$MgSO_4$: 0.15%
Citric Acid: 1.5 mM
$CaCl_2.2H_2O$: 150 $\mu M$
$FeCl_3.6H_2O$: 135 $\mu M$
$MnCl_2.4H_2O$: 75 $\mu M$
$ZnSO_4.7H_2O$: 38 $\mu M$
$CoCl_2.6H_2O$: 15 $\mu M$
$CuCl_2.2H_2O$: 8 $\mu M$
$H_3BO_3$: 8 $\mu M$
$MoO_3$: 15 $\mu M$
Biotin: 1.5 mg/L
Ca Pantothenate: 2.25 mg/L 10 ml of seed culture of *Zymomonas mobilis* ATCC 29191 grown in a medium of the above composition was added to the above fermentation medium. Cultivation was carried out at a temperature of 30° C. with a nitrogen flow of 0.5 SCFH into the culture and with stirring at a rate of 300 rpm. The pH was maintained at 5.5 with 2N KOH.

After 15 hours growth had terminated with the concentration of bacterial cells at 4 g/L (dry weight) and the ethanol concentration at 4.65% (w/v).

After the termination of growth, the second stage of the process was begun by pumping an additional 340 g of glucose dissolved in 600 ml of water into the fermenter vessel over a period of 8.5 hours. Complete utilization of the sugar had occurred by 9.5 hours. The ethanol concentration at the end of the second stage was 11.6%.

EXAMPLE 2

12 liters of a fermentation medium having the following composition were placed in a 14 liter fermenter vessel:
Glucose: 10% (w/v)
Yeast extract (Difco): 1.0%
$KH_2PO_4$: 0.25%
$NH_4Cl$: 0.16%
$MgSO_4$: 0.1%
Citric Acid: 1.0 mM
$CaCl_2.2H_2O$: 100 $\mu M$
$FeCl_3.6H_2O$: 90 $\mu M$
$MnCl_2.4H_2O$: 50 $\mu M$
$ZnSO_4.7H_2O$: 25 $\mu M$
$CoCl_2.6H_2O$: 10 $\mu M$
$CuCl_2.2H_2O$: 5 $\mu M$
$H_3BO_3$: 5 $\mu M$
$MoO_3$: 10 $\mu M$
Biotin: 1.0 mg/L
Ca Pantothenate: 1.5 mg/L 50 ml of seed culture of *Zymomonas mobilis* ATCC 29191 grown in a medium of the above composition was added to the above fermentation medium. Cultivation was carried out at a temperature of 30° C. with a nitrogen flow into the fermenter and with stirring at a rate of 300 rpm. The pH was maintained at 5.5 with 8N KOH.

After growth had terminated, the bacterial cells were collected by centrifugation and resuspended in fresh medium of the above composition to give a bacterial cell concentration of 20 g/L.

1200 ml of the concentrated bacterial cell suspension were placed in a 2 liter fermenter vessel. Stage (ii) of the process was initiated by the addition of 32 ml of a 75% glucose solution to the fermenter. A further 450 ml of 75% glucose was then pumped into the fermenter vessel over the course of 2 hours. Utilization of the sugar was complete after 2.5 hours giving an ethanol concentration of 10.1%.

Stage (ii) of the process was repeated a further four times using the bacterial cells generated by a single stage (i) of the process. After each passage through stage (ii), the bacterial cells were collected by centrifugation and resuspended in 1200 ml of fresh medium of the above composition. Glucose was added in the manner described above for the first passage of the cells through state (ii). In each of the four cycles utilizing the same biomass, the glucose was completely utilized after 2.5 hours with an ethanol concentration of approximately 10% being obtained in each instance.

EXAMPLE 3

Stage (i) of the process was conducted in a 740 ml fermenter containing 320 ml of the fermentation medium described in Example 2 and stage (ii) was conducted in a 2 liter fermenter containing 1740 ml of the same medium.

The stage (i) fermenter was inoculated with 7 ml of seed culture of *Zymomonas mobilis* ATCC 29191 grown in a medium of the composition described in example 2; stage (ii) was inoculated with 12 ml of the same seed culture. Cultivation was carried out at 30° C. with a nitrogen flow into the fermenters and with a stirring rate of 300 rpm. The pH of each fermenter was maintained at 5.5 with 2N KOH.

After growth had terminated two pumps were employed to make the system continuous. The first pump supplied sterile medium containing 12.6% glucose (other components as in Example 2) at a flow rate of 78 ml/hr. Under these conditions, the bacterial cell concentration in the stage (i) fermenter was 4.5 g/L, the ethanol concentration was 5.3% and the residual glucose concentration was 0.6%. The volume of the stage (i) fermenter was maintained at 320 ml by continuously transferring culture to the stage (ii) fermenter at a flow rate of 78 ml/hr. The second pump supplied a sterile 70% glucose solution to the stage (ii) fermenter at a flow rate of 24 ml/hr. giving a total flow in and out of the fermenter of 102 ml/hr. Under these conditions, the bacterial cell concentration in the stage (ii) fermenter was 4.4 g/L, the ethanol concentration was 9.9% and the residual glucose concentration was 1.2%.

EXAMPLE 4

In this example *Zymomonas mobilis* ATCC 29191 was cultured in two fermenters which were operated in tandem in a similar manner as described in Example 3. In this example, however, the biomass contained in the effluent from the second fermenter was retained and added back to the second fermenter. Biomass recycle to the second fermenter was achieved by continuously processing the contents through a Pellicon Ultrafilter Cassette ® (Millipore Corp.) containing 6 sq. ft. of HA type Millipore filters. The culture medium used in this example was of the same composition as examples 2 and 3 except the yeast extract was 0.5% (w/v). The constant volume of the first fermenter (stage (i)) was 1600 ml. It was fed culture medium containing glucose (131 g/L) at a constant rate of 414 ml/hr. The temperature and pH were maintained at 30° C. and 5.5 respectively. The steady-state concentration of biomass in the first fermenter was 4.2 g D.W/L and the ethanol was 5.1% (w/v).

The effluent from the first fermenter was fed continuously and directly to a second fermenter which was operated at a constant volume of 760 ml. A solution of 60% w/v glucose was pumped into the second fermenter at a constant rate of 120 ml/hr. The effluent from the second fermenter was processed through the filtration system with the cells being returned to the second fermenter. The biomass level in the second fermenter was 48 g D.W/L and was kept relatively constant by removing biomass at a rate of about 27 ml/hr. The concentration of ethanol in the cell-free filtrate leaving the system was 10.4% w/v and the residual sugar was 1.7%. Operation of the two stage system at an elevated biomass level in the second fermenter as a consequence of effluent filtration and biomass recycling, resulted in an increased ethanol productivity of the second fermenter (product produced per unit volume per unit time).

I claim:

1. A continuous process for producing ethanol by fermentation in an aqueous medium which comprises cultivating *Zymomonas mobilis* ATCC 29191 in two stages in order to increase ethanol concentration in the fermentation medium, as compared to ethanol concentration in a fermentation medium obtained by continuous cultivation of said *Zymomonas mobilis* microorganism in a single stage, said process consisting essentially of (i) producing a bacterial biomass comprising a cell suspension of said Zymomonas together with ethanol in an ethanol concentration range which does not substantially inhibit production of said Zymomonas cells in a medium containing glucose and a source of nitrogen; and (ii) producing ethanol in the absence of substantial production of said Zymomonas cells, by the addition of a medium containing glucose to the bacterial cell suspension produced in (i), wherein sugar concentration in stage (ii) does not exceed about 6% w/v;

wherein in step (i) the source of nitrogen is a mineral salt medium containing $NH_4+$ ions as the sole source or a mineral salt medium containing $NH_4+$ ions supplemented with an organic source of nitrogen, and ethanol reaches a steady state concentration of about 10% w/v in the biomass in (ii).

2. A process as claimed in claim 1 wherein the two stages of the process are conducted in two fermenters with the bacterial cells produced by a continuous culture in the first fermenter being continuously transferred to a second fermenter.

3. A process as claimed in claim 2 wherein stage (ii) of the process is conducted in a fermenter in which the contents have a substantially constant volume, said fermenter having a continuous feed of the medium required for the second stage of the process.

4. A process as claimed in claim 3 wherein ethanol is recovered from biomass and stage (ii) is repeated up to four times.

5. A process as claimed in claim 2 wherein a portion of the bacterial cells in the second fermenter is removed therefrom and separated from the fermentation broth by continuous filtration or sedimentation and returned to stage (ii) to thereby increase ethanol productivity in stage (ii).

6. A process as claimed in claim 5 wherein stage (ii) is carried out at a temperature of about 28° to 33° C. and at a pH of about 5.5.

7. A process as claimed in claim 6 wherein stage (i) is carried out at a temperature of about 30° C. and a pH of about 5.5.

8. A process as claimed in claim 6 wherein the fermenter in stage (i) and the fermenter in stage (ii) have a working volumetric ratio of about 2:1.

9. A process as claimed in claim 6 wherein ethanol is recovered from biomass and stage (ii) is repeated up to four times.

10. A process as claimed in claim 1 wherein ethanol is recovered from biomass and stage (ii) is repeated up to four times.

* * * * *